United States Patent
Lackey et al.

(10) Patent No.: US 8,709,347 B2
(45) Date of Patent: Apr. 29, 2014

(54) AIR SCENT DISPENSER

(75) Inventors: Robert William Lackey, Hickory, NC (US); Roy Nicholson, Blowing Rock, NC (US); Jeri Lynn Lemke, Hickory, NC (US)

(73) Assignee: Protect Plus Air LLC, Hickory, NC (US)

( * ) Notice: Subject to any disclaimer, the term of this patent is extended or adjusted under 35 U.S.C. 154(b) by 148 days.

(21) Appl. No.: 13/096,414

(22) Filed: Apr. 28, 2011

(65) Prior Publication Data

US 2011/0268615 A1     Nov. 3, 2011

Related U.S. Application Data

(60) Provisional application No. 61/328,743, filed on Apr. 28, 2010.

(51) Int. Cl.
*A61L 9/00* (2006.01)

(52) U.S. Cl.
USPC .............................. 422/123; 239/34; 239/59

(58) Field of Classification Search
CPC .............. A61L 9/03; A61L 9/04; A61L 9/12; A61L 9/125
USPC ................... 422/120–126; 239/34, 58, 47, 59
See application file for complete search history.

(56) References Cited

U.S. PATENT DOCUMENTS

| | | | | | |
|---|---|---|---|---|---|
| 2,765,194 | A | * | 10/1956 | Will | 239/59 |
| 3,902,877 | A | * | 9/1975 | Swaim | 55/490 |
| 4,065,262 | A | * | 12/1977 | Petroff | 96/222 |
| 6,244,518 | B1 | * | 6/2001 | Pogue | 239/36 |
| 6,950,607 | B2 | * | 9/2005 | Yip et al. | 392/395 |
| 7,780,094 | B2 | * | 8/2010 | Caserta et al. | 239/34 |
| 2009/0098026 | A1 | * | 4/2009 | Wood | 422/123 |
| 2009/0212124 | A1 | * | 8/2009 | Kenny | 239/58 |

FOREIGN PATENT DOCUMENTS

EP            1561477 A1 *  8/2005  ............... A61L 9/04

* cited by examiner

*Primary Examiner* — Kevin Joyner
*Assistant Examiner* — Liban Hassan
(74) *Attorney, Agent, or Firm* — Clements Bernard PLLC

(57) ABSTRACT

The present invention provides a scent dispenser device for positioning adjacent an air filter for infusing the air passing through the air filter with a scent that includes an air filter and a scent dispenser device. The scent dispenser device further includes a base having a bore for allowing air to flow through the base, a valve having at least one air passageway for allowing air to flow through the valve from the base, a scented media disposed within the base, and a cap that is rotationally engaged to the valve and controls the flow of air into base.

20 Claims, 6 Drawing Sheets

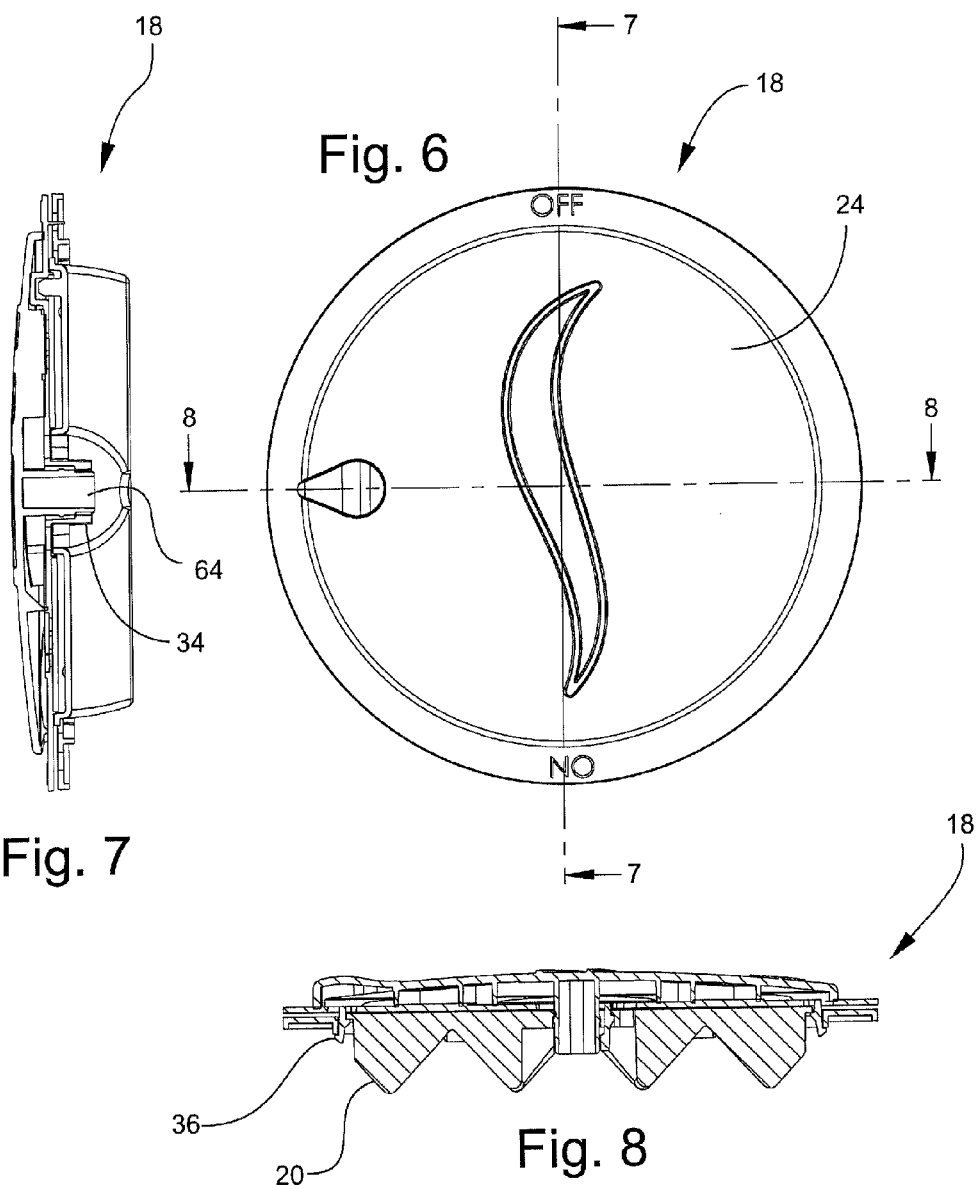

AIR SCENT DISPENSER

CROSS REFERENCE TO RELATED PATENT APPLICATION

The current application claims the benefit of the earlier priority filing date of the provisional application Ser. No. 61/328,743, that was filed on Apr. 28, 2010.

FIELD OF THE INVENTION

The present invention relates generally to an air filter scent dispenser device and more specifically relates to a scent dispenser device that is engaged to an air filter for infusing the air passing through the air filter with scent, which is carried throughout the HVAC ductwork and into the habitable portions of a structure.

BACKGROUND OF THE INVENTION

In any place where people gather there will be various odors, fragrances and the like. It is common for homeowners and businesses to oftentimes struggle to maintain pleasant smelling environments. Many odors from such various things as cooking, personal hygiene products, the presence of pets, and cigarette smoke can be present in a home or business. Odors of these types are often difficult to combat. As such, a large industry has developed dedicated to the removal and/or masking of these odors. Products such as scented sprays, odor eliminating cleaning products, fans, and air purifiers and filters are now commonly found in homes and businesses. In addition, scent dispersion products such as scented candles and electric scent dispersers are now commonly used and widely available.

Despite the wide variety of readily available devices, products, and apparatuses available to help control or eliminate odors, each and every product suffers from the same limitation, its use is localized to a particular vicinity of use. Specifically and by way of example, use of a scented spray only affects the area in which the spray is used. So, another room in the house or business will not be affected by spraying a scented spray in a separate room. Likewise, electric scent dispersers and candles are only able to disperse scents in the room in which they are used. If one desires to disperse scents in multiple locations or rooms, one must use a product or device in each room. This is both time consuming and expensive.

Thus, a need exists for a device or product that is able to disperse a scent into all rooms in a home or business simultaneously. Further, a product is needed that allows a homeowner or business proprietor to selectively dispense scents into the premises with the ability to control the amount of scent dispersed. Still further, a need exists for a product that can remove odors or scents from the entire home or business without having to be transported from one room to another.

BRIEF SUMMARY OF THE INVENTION

A preferred embodiment of the present invention includes a scent dispenser device that includes a base, a scented media disposed within the base, a cap, and a valve for allowing air to flow into the base.

In another preferred embodiment of the present invention, the scent dispenser device includes a retention ring positioned on an air filter for receiving the scent dispenser device and retaining the scent dispenser device to the air filter.

In yet another preferred embodiment of the present invention, the scent dispenser device includes a base that contains at least one trough for receiving the scented media.

In yet another preferred embodiment of the present invention, the scent dispenser device includes a cap that contains a post that is received within the valve for rotationally engaging the cap to the valve.

In yet another preferred embodiment of the present invention, the scent dispenser device includes a valve that contains a second air passageway or grill for allowing air to flow through the valve.

In yet another preferred embodiment of the present invention, the scent dispenser device includes a valve that contains at least one inner resiliently flexible finger for engaging the valve to the base.

In yet another preferred embodiment of the present invention, a scent dispenser device for positioning adjacent an air filter for infusing the air passing through the air filter with a scent includes an air filter and a scent dispenser device. The scent dispenser device includes a base having a bore for allowing air to flow through the base, a scented media disposed within the base, a valve having at least one air passageway for allowing air to flow through the valve from the base and a second air passageway for allowing air to flow into the base and contact the scented media, and a cap that is rotationally engaged to the valve and controls the flow of air into the base.

In yet another preferred embodiment of the present invention, the scent dispenser device includes a second air passageway that is a grill disposed on the valve for allowing air to flow into the base and prevents the scented media from exiting the base.

In yet another preferred embodiment of the present invention, the scent dispenser device includes a plurality of beads disposed within the base.

In yet another preferred embodiment of the present invention, the scent dispenser device includes a scented polypropylene disposed within the base for infusing the air with scent.

In yet another preferred embodiment of the present invention, the scent dispenser device includes a base with a plurality of troughs for receiving the scented media.

In yet another preferred embodiment of the present invention, the scent dispenser device includes a base that includes a bore with a plurality of retention slots positioned around the bore and the valve contains a plurality of inner resiliently flexible fingers that are received within the retention slots for engaging the valve to the base.

In yet another preferred embodiment of the present invention, a scent dispenser device for positioning adjacent an air filter for infusing the air passing through the air filter with a scent includes an air filter and a scent dispenser device. The scent dispenser device includes a base having a bore for allowing air to flow through the base, a scented media disposed within the base, a valve having at least one air passageway for allowing air to flow through the valve from the base and a second air passageway disposed on the valve for allowing air to flow into the base and contact the scented media, and a cap that is rotationally engaged to the valve and controls the flow of air into the base. The valve may be rotated from a first position to a second position, wherein the first position prevents air from flowing through the second air passageway and into the base and the second position allows air to flow through the second air passageway and into the base.

In yet another preferred embodiment of the present invention, the scent dispenser device includes a stop positioned on the valve for preventing rotational movement of the cap at a predetermined location.

In yet another preferred embodiment of the present invention, the scent dispenser device includes outer resiliently flexible fingers positioned on the outer edge of the valve for engaging the base and forming an engaged arrangement between the valve and the base.

In yet another preferred embodiment of the present invention, the scent dispenser device includes at least one post disposed on the underside of the valve and a retention ring engaged to the air filter containing at least one bore for receiving the at least one post for engaging the scent dispenser device to the air filter.

BRIEF DESCRIPTION OF THE DRAWINGS

The present invention is illustrated and described herein with reference to the various drawings, in which like reference numbers denote like method steps and/or system components, respectively, and in which:

FIG. 6 is a top view of the scent dispenser device;

FIG. 7 is a side, cross-sectional view of the scent dispenser device along the line 7-7 of FIG. 6; and FIG. 8 is another side, cross-sectional view of the scent dispenser device along the line 8-8 of FIG. 6.

DETAILED DESCRIPTION OF THE INVENTION

Figure 1:
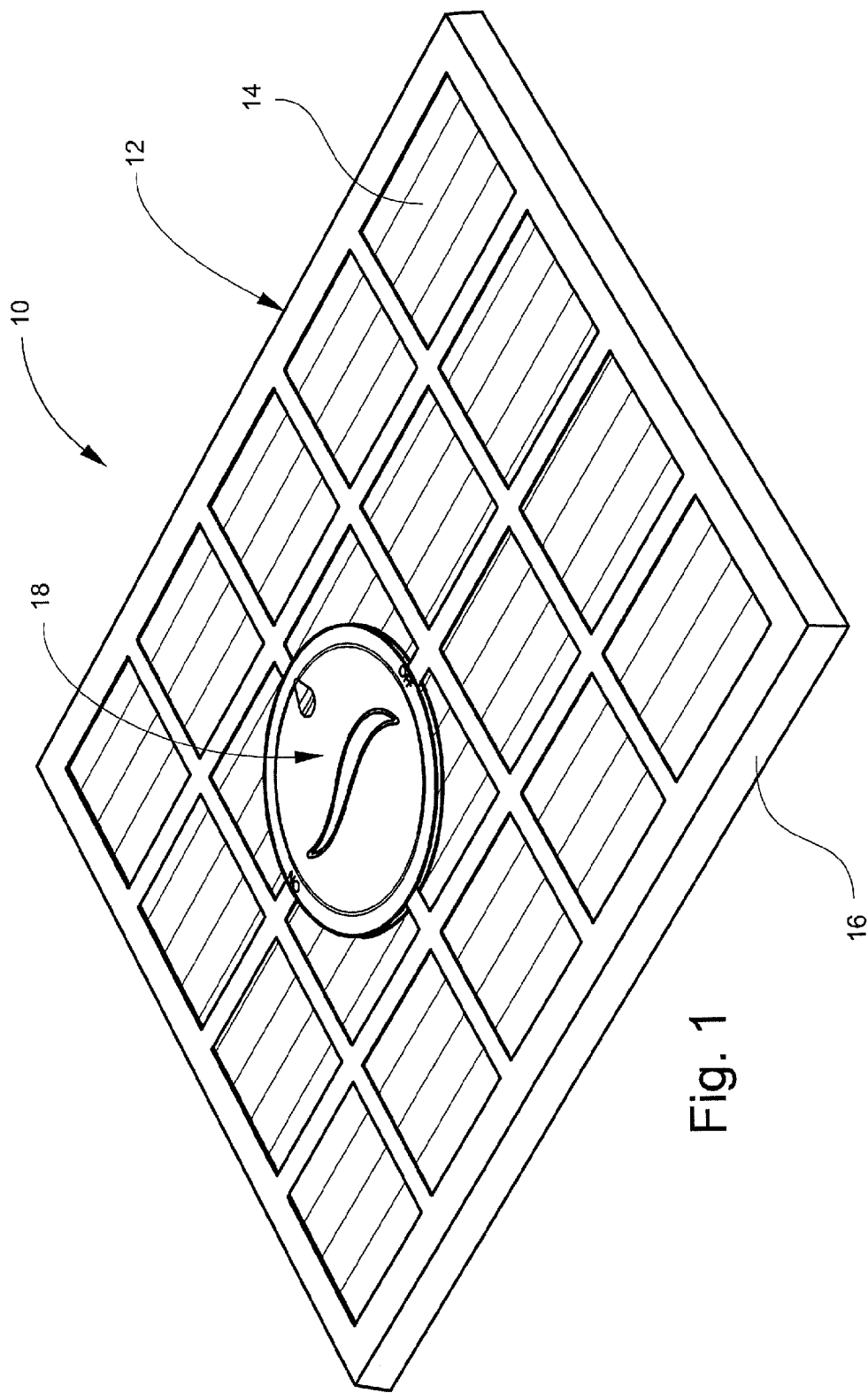
FIG. 1 is a perspective view of an air filter and scent dispenser device of the present invention.

Referring now specifically to the drawings, a scent dispenser device for engagement to an air filter is illustrated in FIG. 1 and collectively shown generally at reference numeral 10. The air filter 12 comprises a media 14 that is composed of a non-woven web for blocking particulate matter carried by the air through common HVAC ductwork. The media 14 is folded in accordion fashion to form a plurality of V-shaped pleats, and is housed in a rectangular, paper-board frame 16. The scent dispenser device 18 comprises a base 20, a valve 22, and a cap 24.

The base 20 of the scent dispenser device 18 may contain a plurality of troughs 26. The troughs 26 may be aligned side-by-side and serve as the bottom portion of the base 20. The apex of each trough 26 may be engaged to a circular rim forming the top portion of the base 20. A locking hub 28 is positioned within the center of the base 20 and contains a centrally located bore 30 and retention slots 32. The retention slots 32 are spaced an equal-distance around the bore 30. As illustrated, the locking hub 28 may contain three equally, spaced-apart retention slots 32 around the bore 30, but any number of retention slots 32 may be disposed on the locking hub 28 depending upon the desires of the user.

The base 20 is designed to retain a scented media, such as scented beads or scented polypropylene. The troughs 26 as described above are best equipped to retain a plurality of scented beads within the trough. As air passes through the troughs 26 and over the beads, the air is infused with scent that then exits the scent dispenser device 18.

In another alternative embodiment, the bottom portion of the base 20 may be relatively flat to retain scented polypropylene, which could be in disk or strip form. The beads may possess the same scent or may have different scents that when mixed together produce a pleasant aroma. Alternatively, the scented polypropylene may contain only one scent, but may also contain multiple scents that when mixed together produce a pleasant aroma. In another alternative embodiment, the scented media may be oils, gels, molded pads, and the like.

Figure 4:
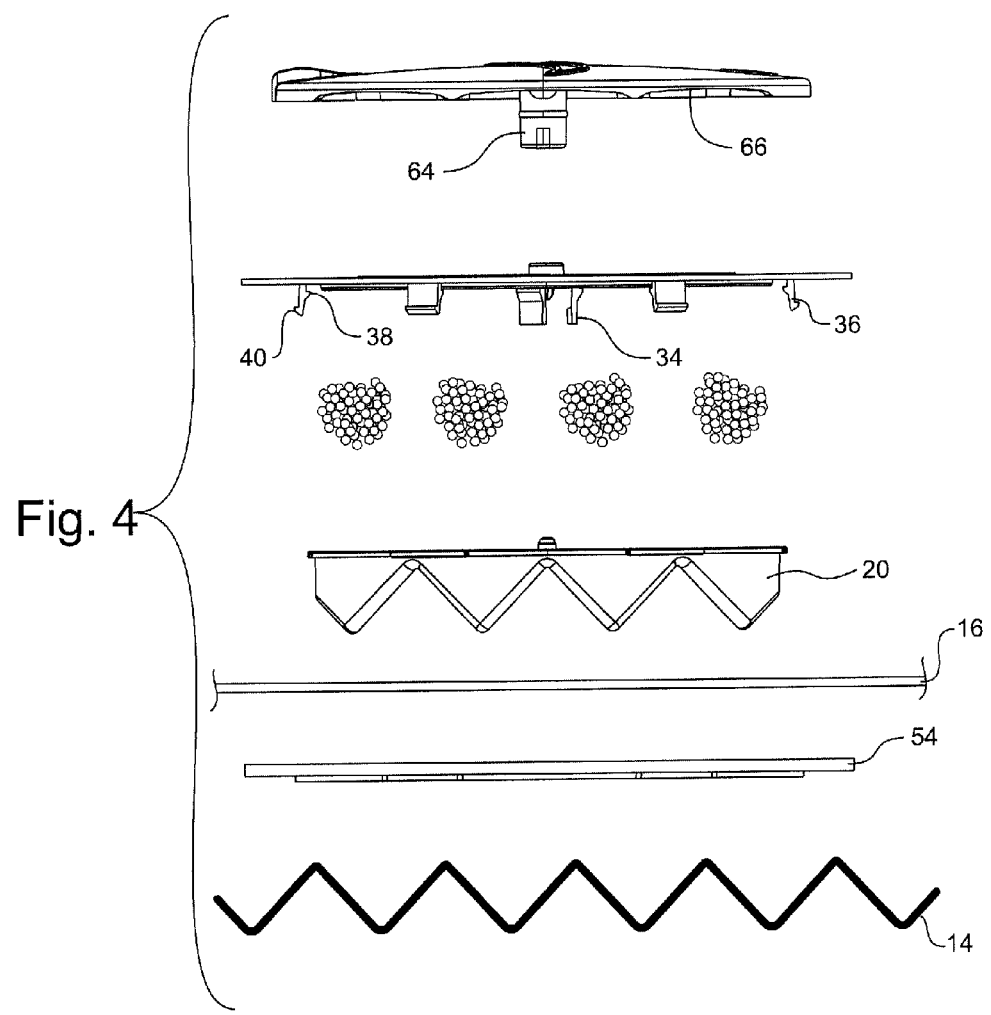
FIG. 4 is a side exploded view of the air filter and scent dispenser device of the present invention.

The valve 22 is a generally cylindrical disk that is engaged to the base 20 includes a plurality of inner resiliently flexible fingers 34 and a plurality of outer resiliently flexible fingers 36. The inner resiliently flexible fingers 34 are positioned in close proximity to the center point of the valve 22. The outer resiliently flexible fingers 36 are positioned in close proximity to the outer edge of the valve 22. Each flexible finger (34, 36) has an upper portion and a lower portion and contains an inner collar 38 and an outer collar 40, as shown in FIG. 4. The upper portion of the flexible finger (34, 36) is engaged to the valve 22 and the bottom portion extends perpendicularly downward from the valve 22. The outer collar 40 is positioned in close proximity to the lower portion of the flexible finger (34, 36). The inner collar 38 is positioned between the lower portion and the upper portion of the resiliently flexible finger (34, 36). The inner resiliently flexible fingers 34 are designed to be selectively secured to the base 20 and are positioned within the retention slots 32 disposed around the bore 30 of the locking hub 28.

The valve 22 is generally circular in shape and the outer portions of the valve 22 extend beyond the periphery of the cap 24. The valve 22 may contain directions or instructions, as illustrated in FIGS. 1 and 6. As shown in FIGS. 1 and 6, the valve 22 contains the terms "on" and "off." These terms refer to the position of the cap 24 for allowing air to flow over the scented media contained within the base 20 and for preventing air from flowing through the scented media. When the indicator tab 42 of the cap 24 is positioned in the "on" position, air is allowed to flow through the scented media contained within the base 20 and the air is infused with scent. When the indicator tab 42 of the cap 24 is positioned in the "off" position, air is prevented from flowing through the scent media and the air is not infused with scent. A stop 44 is disposed on the valve 22 that engages a rib 46 disposed on the underside of the cap 24. The stop 44 prevents the cap 24 from rotating 360°. Instead, the stop 44 only allows the cap 24 to rotate 180° between the "on" and the "off" position. In another alternative embodiment, the cap 24 is stationary and positioned in the "on" position at all times, meaning air is allowed to flow through the scented media contained within the base 20 and the air is infused with scent.

Figure 5:
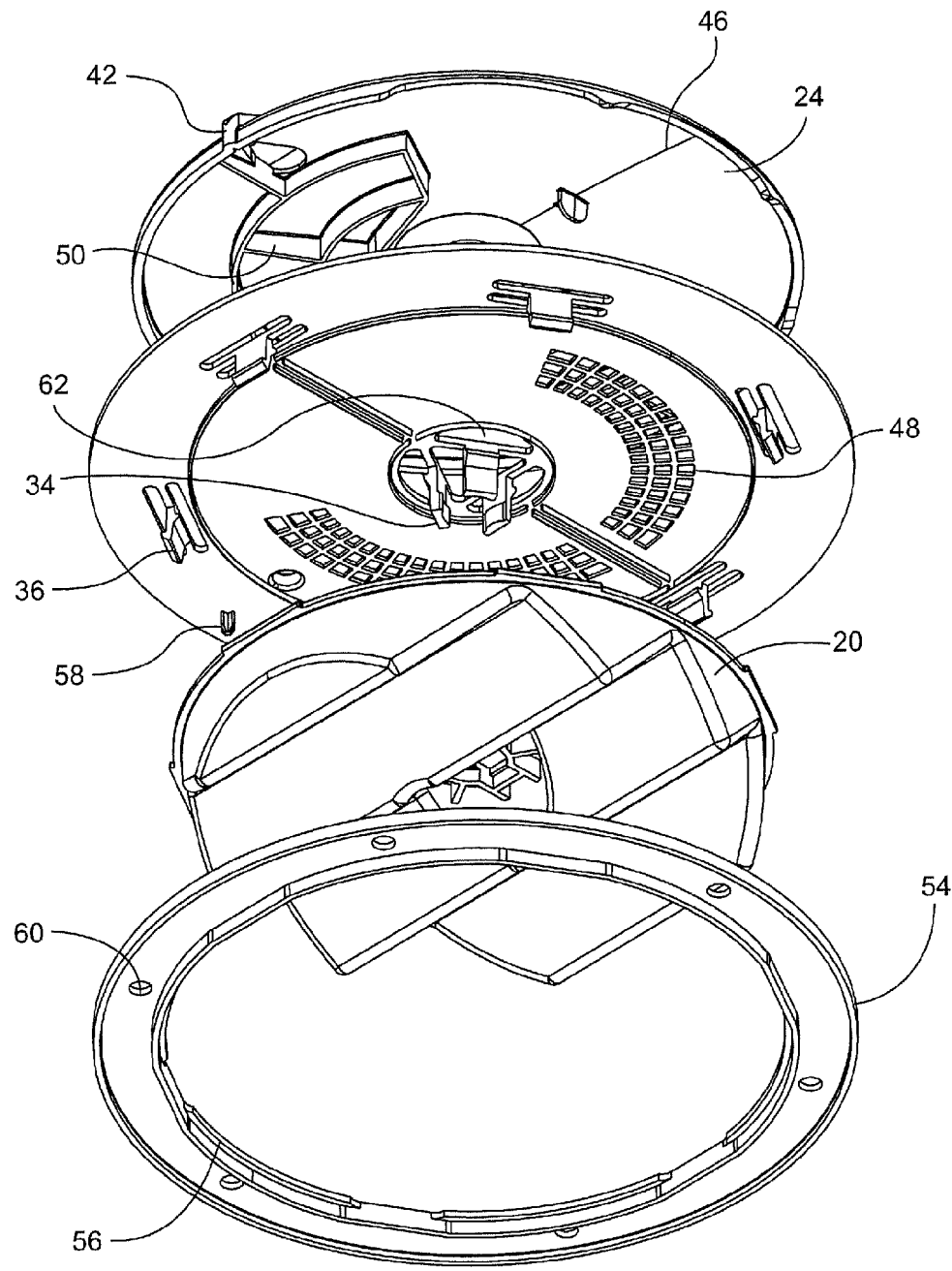
FIG. 5 is another exploded perspective view of the scent dispenser device of the present invention.

As illustrated in FIG. 5, the valve 22 contains a second air passageway 48 that opens into the base 20. As illustrated, the second air passageway 48 takes the form of a grill 48, having a criss-cross structure. The grill 48 is positioned on a half of the valve 22 and is semi-circle in shape. The grill 48 allows air to flow through the base 20 and over the scented media. A grill 48 is illustrated but any passageway that allows air to flow is acceptable. The grill 48 allows air to flow into the base 20, while also retaining the scented media, particularly scented beads, within the base 20. The cap 24 contains a cover 50 positioned on the underside of the cap 24. The cover 50 is composed of raised ribs and entirely covers the grill 48 when the cap 24 is in the "off" position. In other words, when the cap 24 is in the "off" position, the cover 50 is over-top and completely covers the grill 48, thus preventing any air flow through the grill 48. As the cap 24 is rotated to the "on" position, the cover 50 is removed from the grill 48 incrementally, thus allowing air to flow through the grill 48. When the cap 24 is rotated to the "on" position, the cover 50 is completely removed from the grill 48, thus allowing unrestricted air flow through the grill 48. A user may adjust the amount of scent in the air by rotating the cap 24 between the "on" position and the "off" position.

In another alternative embodiment and as described above, the scented media may have different scents that when mixed together produce a pleasant aroma. In this embodiment, each scented media is contained within a separate compartment or separate trough 26 within the base 20. In other words, a scented media is disposed within one trough 26 of the base 20, and a different scented media is disposed within a second trough 26 of the base 20. The second air passageway or grill 48 covers each trough 26. As the cap 24 is rotated to the "on" position, the cover 50 is removed from the grill 48 incrementally, thus allowing air to flow through the grill 48. By way of example only, when the cap 24 is rotated 45°, the cover 50 is removed from the grill 48 and exposes only one trough 26 containing a scented media. It will be known to one of ordinary skill in the art, that the rotation of the cap 24 any degree may expose one of the troughs 26 and the amount of rotation can vary depending upon the desires of the user. By way of example only, when the cap 24 is rotated 90°, the cover 50 is removed from the grill 48 and exposes the second trough 26 containing the other scented media. It will be known to one of ordinary skill in the art, that the rotation of the cap 24 any degree may expose the second trough 26, in addition to the first trough 26, and the amount of rotation can vary depending upon the desires of the user. When the cap 24 is rotated to the "on" position, the cover 50 is completely removed from the grill 48, thus allowing unrestricted air flow through the grill 48 and both troughs 26, exposing both of the scents contained on the scented media.

The frame 16 of the air filter 12 includes a grid that covers the back side of the media 14. The back side is meant to refer to the side opposite the direction of air flow. The grid, as shown in FIG. 1, consists of parallelograms, generally rectangular or square shapes. A single circular area is positioned within the grid for receiving the scent dispersion device 18. A retention ring 54 is positioned between the media 14 and the circular area of the grid of the frame 16. The retention ring 54 is designed to receive the scented dispersion device 18. The retention ring 54 contains a plurality of inner ledges 56 that are designed to receive the outer resiliently flexible fingers 36 of the valve 22. The outer collar 40 of the outer resiliently flexible finger 36 engages the inner ledge 56, forming a selectively secured arrangement. The inner collar 38 of the outside resiliently flexible finger engages the outer edge of the base 20, as shown in FIGS. 7 and 8. As illustrated in FIG. 5, the inner ledges 56 are spaced-apart and equal-distance around the inner periphery of the retention ring 54. The retention ring 54 and circular area of the grid may contain corresponding retention bores 60 for receiving a retention pin 58 that is disposed on the underside of the valve 22. When the retention pin 58 is inserted into the retention bores 60 disposed on the retention ring 54 and circular area of the grid, the scent device 10 is retained to the air filter 12.

Figure 2:
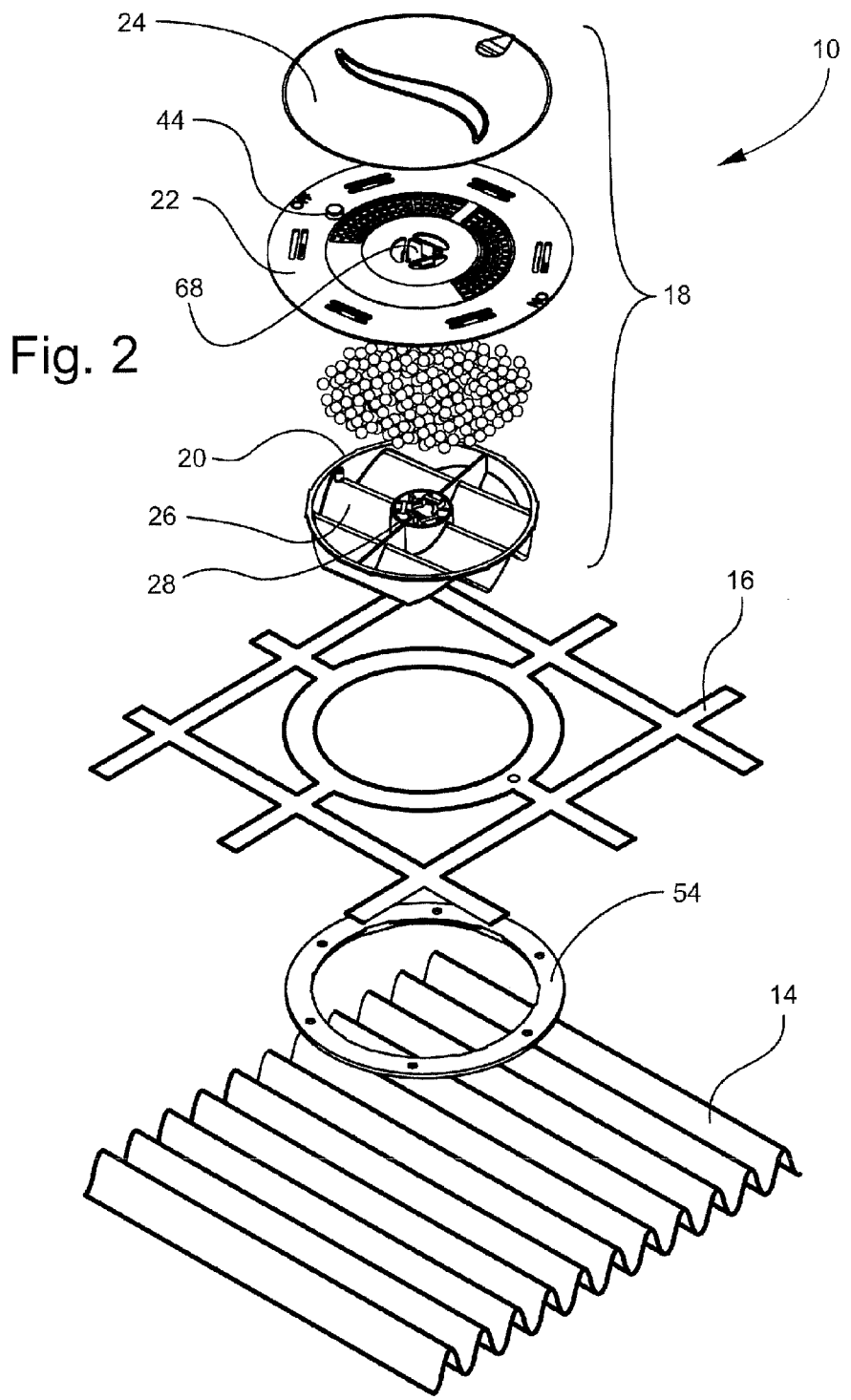
FIG. 2 is an exploded view of an air filter and scent dispenser device of the present invention.

The valve 22 contains a centrally located bore 8 with at least one first air passageway 62 disposed adjacent the bore 8. As illustrated in FIG. 2, three spaced-apart first air passageways 62 are disposed adjacent the bore 8. It will be known to one of ordinary skill in the art that any number of first air passageways 62 may be disposed adjacent the bore 8 for allowing air to pass through the valve 22. The bore 8 is designed to receive a post 64 disposed perpendicularly downward from the cap 24. The post 64 is positioned within the bore 608 in a rotationally secure arrangement allowing the cap 24 to rotate with respect to the valve 22.

Figure 3:
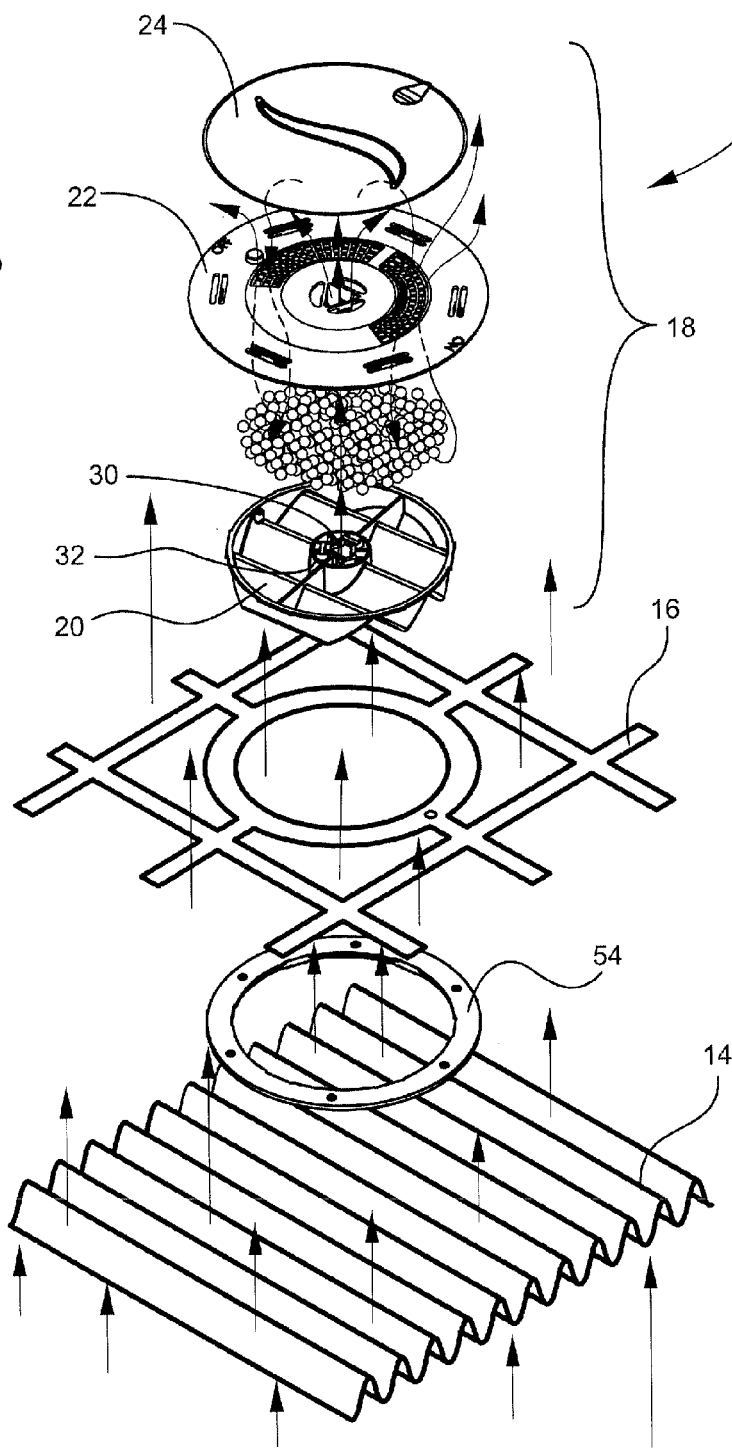
FIG. 3 is an exploded view illustrating the air travel through the air filter and scent dispenser device of the present invention.

FIG. 3 illustrates the direction of air flow through the scent device 18. Air flows through the media 14 of the air filter 12 and a portion of the air flows through the bore 30 of the base 20. Afterwards, the air then progresses through the first air passageways 62 of the valve 22 and contacts the underside of the cap 24. The air then ricochets downwards through the grill 48 (assuming the cap 24 is in the "on" position or is allowing air to flow through the grill 48) and the air contacts the scented media, such as scented beads, located in the troughs 26 of the base 20. After the air is infused with scent, the air travels upward through the grill 48 and then exits the scent device 18 through at least one arcuate exit hole 66 disposed on the side of the cap 24. If the cap 24 is in the "off" position, the air is prevented from entering the grill 48 and the base 20; therefore, the air travels out of the arcuate exit hole 66 without being infused with scent and traveling through the grill 48 and base 20.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A scent dispenser device, comprising:
   a base containing a locking hub positioned within a center of the base, wherein the locking hub contains a centrally located bore and at least one retention slot disposed adjacent the bore;
   a scented media disposed within the base
   a cap with a top side and a bottom side;
   a first air passageway that directs air towards the cap without passing through the scented media; and
   a generally cylindrical valve containing a second air passageway for allowing air to flow into the base and at least one resiliently flexible finger having an upper portion and a lower portion, wherein the upper portion is engaged to the valve and the lower portion is selectively secured to the at least one retention slot;
   whereby the air in the first air passageway contacts the bottom side of the cap which causes the air to change direction and flows through the second air passageway and into the base.

2. The scent dispenser device of claim 1, further comprising a retention ring engaged to the scent dispenser device and disposed on an air filter for receiving the scent dispenser device and retaining the scent dispenser device to the air filter.

3. The scent dispenser device of claim 1, wherein the base contains at least one trough for receiving the scented media.

4. The scent dispenser device of claim 1, wherein the cap is rotationally engaged to the valve.

5. The scent dispenser device of claim 1, wherein the valve contains a first air passageway for allowing air to flow through the valve.

6. The scent dispenser device of claim 1, wherein the valve contains a plurality of inner resiliently flexible fingers that extend perpendicularly downward from the valve and the lower portion contains an outer collar for selectively securing the valve to the at least one retention slot of the base.

7. A scent dispenser device for positioning adjacent an air filter for infusing the air passing through the air filter with a scent, comprising:
   an air filter;
   a scent dispenser device; comprising;
   a base containing a locking hub positioned within a center of the base, wherein the locking hub contains a centrally located hollow bore for allowing air to flow through the bore; a scented media disposed within the base;
   a valve having at least one first air passageway for allowing air to flow through the valve from the base and a second air passageway for allowing air to flow into the base and contact the scented media; and
   a cap having a first side and a second side that is rotationally engaged to the valve and controls the flow of air into base;
   whereby the valve contains an outer portion that extends beyond the periphery of the cap and air is directed through the bore of the base and through the first air passageway of the valve wherein the air contacts the second side of the cap, causing the air to proceed through a second air passageway of the valve and into the base.

8. The scent dispenser device of claim 7, wherein the second air passageway is a grill disposed on the valve for allowing air to flow into the base and preventing the scented media from exiting the base.

9. The scent dispenser device of claim 7, further comprising a plurality of scented beads disposed within the base.

10. The scent dispenser device of claim 7, further comprising a post engaged to the cap and received within a bore of the valve for rotationally engaging the cap to the valve.

11. The scent dispenser device of claim 7, further comprising scented polypropylene disposed within the base for infusing the air with scent.

12. The scent dispenser device of claim 7, further comprising a retention ring engaged to the scent dispenser device and engaged to the air filter for receiving the scent device and engaging the scent device to the air filter.

13. The scent dispenser device of claim 7, wherein the base contains at least one trough for receiving the scented media.

14. The scent dispenser device of claim 7, wherein the base contains a plurality of troughs for receiving the scented media.

15. The scent dispenser device of claim 7, wherein the base contains a bore with a plurality of retention slots positioned around the bore and the valve contains a plurality of inner resiliently flexible fingers that are received within the retention slots for engaging the valve to the base.

16. A scent dispenser device for positioning adjacent an air filter for infusing the air passing through the air filter with a scent, comprising:
   an air filter; a scent dispenser device; comprising,
   a base containing a locking hub positioned within a center of the base, wherein the locking hub contains a centrally located hollow bore for allowing air to flow through the bore;
   a scented media disposed within the base;
   a valve having at least one first air passageway for allowing air to flow through the valve from the bore of the base, without passing through the scent media, and a second air passageway disposed on the valve for allowing air to flow into the base and contact the scented media; and
   a cap that is rotationally engaged to the valve and controls the flow of air into base and the cap may be rotated from a first position to a second position, wherein the first position prevents air from flowing through the second air passageway and into the base and the second position allows air to flow through the second air passageway and into the base.

17. The scent dispenser device of claim 16, further comprising a stop positioned on the valve for preventing the rotational movement of the cap at a predetermined location.

18. The scent dispenser device of claim 16, further comprising outer resiliently flexible fingers positioned on the outer edge of the valve for engaging the base and forming an engaged arrangement between the valve and the base.

19. The scent dispenser device of claim 16, further comprising at least one post disposed on the underside of the valve and a retention ring engaged to the air filter containing at least one bore for receiving the at least one post for engaging the scent dispenser device to the air filter.

20. The scent dispenser device of claim 16, wherein the base contains troughs aligned side-by-side for receiving the scented media and serve as the bottom of the base and each trough has an apex that engages a circular rim forming the top portion of the base.

* * * * *